United States Patent [19]
Diener

[11] Patent Number: 6,152,870
[45] Date of Patent: Nov. 28, 2000

[54] ENDOSCOPE

[75] Inventor: Jörg Diener, Oberderdingen, Germany

[73] Assignee: Richard Wolf GmbH, Knittlingen, Germany

[21] Appl. No.: 09/105,376

[22] Filed: Jun. 26, 1998

[30] Foreign Application Priority Data

Jun. 27, 1997 [DE] Germany ............ 197 27 419

[51] Int. Cl.$^7$ ........................................ A61B 1/00
[52] U.S. Cl. .................. 600/107; 600/104; 600/106; 600/153; 600/154
[58] Field of Search .................. 600/104, 106, 600/107, 109, 130, 145, 146, 153, 154, 160, 162

[56] References Cited

U.S. PATENT DOCUMENTS

| | | | |
|---|---|---|---|
| 4,407,273 | 10/1983 | Ouchi | 600/107 |
| 4,452,236 | 6/1984 | Utsugi | 600/107 |
| 4,949,706 | 8/1990 | Thon | 600/107 |
| 5,343,853 | 9/1994 | Komi | 600/107 |

FOREIGN PATENT DOCUMENTS

| | | |
|---|---|---|
| 1 766 695 | 4/1971 | Germany . |
| 77 06 935 | 8/1977 | Germany . |
| 79 31 192 | 11/1979 | Germany . |
| 36 21 509 | 3/1988 | Germany . |
| 44 32 677 | 3/1996 | Germany . |
| 195 37 812 | 1/1997 | Germany . |
| 2 004 749 | 4/1979 | United Kingdom . |

*Primary Examiner*—Linda C. M. Dvorak
*Assistant Examiner*—Brad C. Blaise
*Attorney, Agent, or Firm*—Cohen, Pontani, Lieberman & Pavane

[57] ABSTRACT

An endoscope comprises a hollow shank, optic viewing means positioned in the hollow shank for observing a body cavity, and a separate adjustable instrument channel which is axially, slidably arranged in an internal guiding region of the hollow shank. The instrument channel has a flexible curvature section and a laterally running end section with an end portion that is pivotably and articulably mounted in a radial passage in the distal circumferential wall region of the hollow shank. Sliding the instrument channel axially in the hollow shank results in flexing of the curvature section and pivoting of the end portion, such that an auxiliary instrument provided in the instrument channel is laterally deflected when guided through the hollow shank.

6 Claims, 2 Drawing Sheets

ENDOSCOPE

BACKGROUND OF THE INVENTION

The invention is directed to an endoscope for application in cavities in combination with a flexible auxiliary instrument.

Such an endoscope is described in the German Utility Model 77 06 935. In a hollow shank with a distal lateral exit view there is located an optical as well as illuminating means for observing a cavity to be examined, an axial guide-through space for a flexible auxiliary instrument, distal deflecting means for deflecting an auxiliary instrument introduced into the hollow shank and proximally handled operating rods for operating the distal deflecting means in order to move the free end of the auxiliary instrument into a radial operating position. The deflecting means distally comprise a so-called Albarran lever which is pivoted by way of operating rods, and the free end of the auxiliary instrument is more or less pressed radially outwards. Deflecting designs using Albarran levers however require a significant amount of space and limit the reduced constructional manner of an endoscope shank, i.e. a reduction in the shank diameter. Furthermore with an Albarran lever it is essentially not possible to deflect the free end of an auxiliary instrument introduced into the endoscope shank beyond a right angle towards the rear, thus retrograde. Certain regions of cavities therefore may not be reached with such an endoscope or reached only with a complicated handling of the endoscope. This applies in particular to cavities in rigid bodies which comprise an rigid inspection passage for the endoscope which is small in diameter, i.e. with technical devices.

In the German Utility Model 79 31 192 an insert for a rectoscope head is described. This insert comprises, besides two channels for the introduction of air and rinsing water, a channel with an optics means for distal straight ahead viewing as well as an instrument channel for an auxiliary instrument whose distal flexibly formed end region is deflectable in a certain angular region towards the optics channel. All channels are held together by way of common rings. Although this insert comprises a channel for an auxiliary instrument, i.e. a probe, the deflectable end of the instrument channel may not be deflected laterally outwards but only laterally inwards since the working region of the auxiliary instrument is located axially in front of the insert. A retrograde carrying out of operations laterally next to the insert in a cavity to be examined is thus not possible.

In the German patent 195 37 812 there is described a technoscope with a distal lateral exit view. It comprises a hollow shank with an optics and illuminating means and with an instrument carrier at the distal shank end, which is equipped with exchangeable instruments, e.g. with measuring and machining tools, and is pivotable from an introduction position in which it is flush with the hollow shank, into an operating position deflected at right angles to the shank, as well as proximally operable operating means and drive means running through the hollow shank for bringing into position or for driving the instrument carrier and thus the working means concerned. With the help of a measuring tool for longitudinal measurements, e.g. the extent of damage to turbine blades with respect to area may be evaluated since on turbine housings there are provided inspection openings for endoscopic examinations and small repairs. Apart from the fact that this pivotable instrument carrier with exchangeable working means including its operating and drive means conflicts with a miniturized constructional manner of the technoscope shank, it is also not possible with this technoscope to adjust the instrument carrier and thus the working means beyond a right angle in a retrograde direction.

BRIEF SUMMARY OF THE INVENTION

The object of the invention lies in the improvement of an endoscope of the previously cited type to the extent that the auxiliary instrument introduced into the cavity with the help of an endoscope, by way of a simplified deflecting constructional manner in the distal endoscope region, can be brought into a retrograde working position reaching beyond 90°.

By way of the solution according to the invention, the components taking up much space in the distal end region of the hollow shank together with their relatively complicated operating means, as deflecting means for an auxiliary instrument introduced into the endoscope, for example a measuring probe, are done away with. By way of this it is possible for endoscopes with a smaller diameter of the hollow shank to be manufactured. Furthermore the movable mounting of the distal end of the instrument channel according to the invention allows for the section of the auxiliary instrument protruding from this channel to be pivoted retrogradely beyond 90°. In this way also regions in cavities are accessible for examination and where appropriate for treatment, which up to now could not be reached or could only be reached with great difficulty.

Thus e.g. the free ends of blades in engine turbines may be better examined for possible damage, since they can be more easily viewed. Also the operation of the auxiliary instrument is simplified since the instrument channel only needs to be moved to and fro in the hollow shank from the proximal side of the instrument in order to pivot the auxiliary instrument which protrudes by a certain amount out of the instrument channel. Instead of the measuring probe, a spray nozzle, for example for incorporating a fluorescence agent, may be introduced as an auxiliary instrument into the technical cavity.

In one advantageous formation of the invention the radial passage at the distal hollow shaft region comprises a circumferential-like concave bearing surface, wherein the end of the distal end section of the instrument channel is provided with a formation gliding on the concave bearing surface. By way of this a particularly simple pivoting bearing of the distal instrument channel end is made possible.

The sliding formation of the instrument channel end may consist of a circumferential groove with an elastic ring element contained therein. By way of this it is achieved that apart from a slight pivotability of the instrument channel end also a sealing to the inside of the endoscope shank is created in order to prevent the penetration of dirt particles.

In order to be able to pivot the end of the distal end section of the instrument channel in the longitudinal direction of the hollow shaft in a defined manner, two bearing pins which lie diametrically opposite transversely to the longitudinal direction of the hollow shaft and which are flush with one another may be provided, these on the one side engaging into the distal instrument channel end and on the other side into the walling of the radial passage.

For the stabilized longitudinal movement of the instrument channel in the hollow shank, guiding means, for example in the form of tubular inserts, may be provided. Such guiding means are particularly advantageous when it is the case of a flexible endoscope. In this case the instrument channel is likewise flexible over on its whole length.

BRIEF DESCRIPTION OF THE DRAWINGS

The invention is hereinafter described in more detail by way of one embodiment example shown in the accompanying drawings. There are shown.

DETAILED DESCRIPTION OF THE INVENTION

Figure 1:
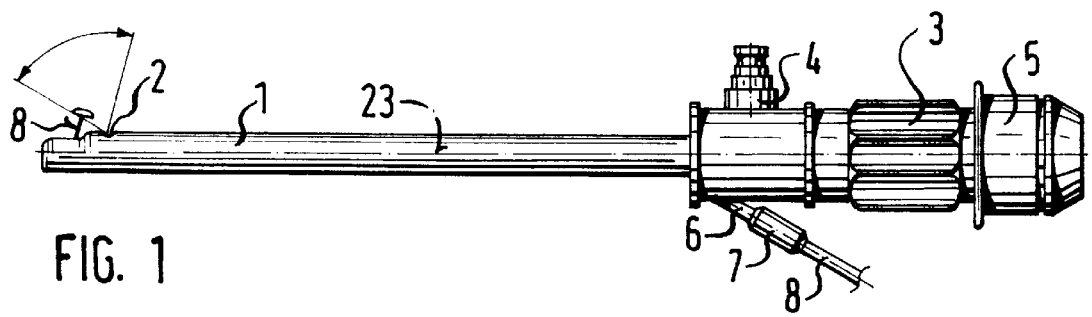
FIG. 1: a lateral view of the whole endoscope.

The endoscope shown in FIG. 1 comprises a hollow shaft 1 with a distal lateral exit view window 2 and a proximal handle 3 which is provided with a fiberoptic connection 4 and with an ocular funnel 5. From a lateral exit of the handle 3 protrudes the proximal end section of an instrument channel 6 which extends in the hollow shank 1 and whose free end is provided with an operating part 7. Through the instrument channel 6 there is guided a flexible auxiliary instrument 8, e.g. a measuring probe, which protrudes laterally from the shank 1 when it is situated in the working position.

Figure 2:
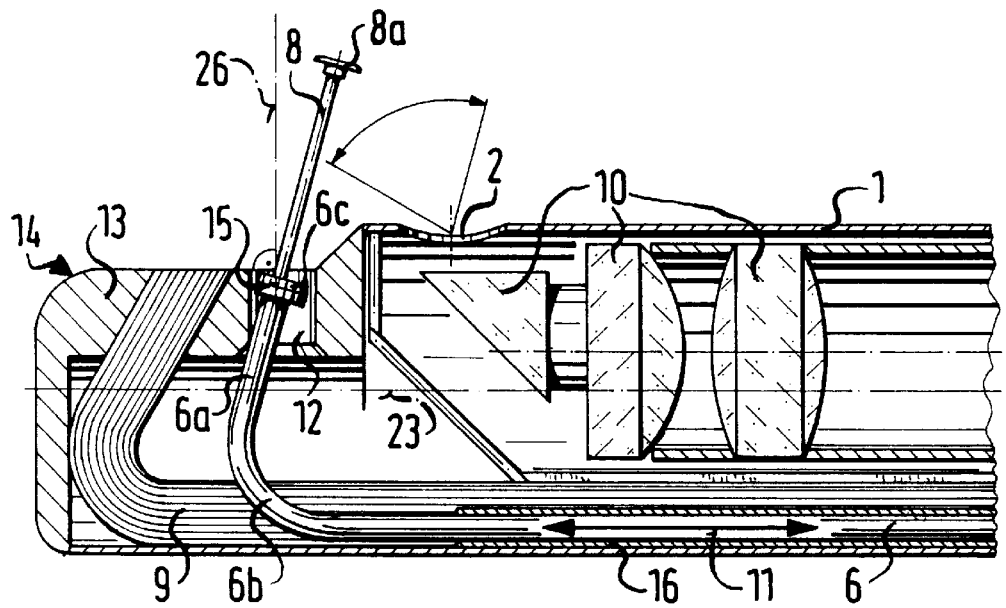
FIG. 2: a sectional representation on the distal end region of the endoscope in an enlarged scale.

From the part representation according to FIG. 2 is can be seen that in the inside of the hollow shank 1 in the known manner fiber-optic fibers 9 and an optical system 10 are provided for the lateral exit view window 2, in order to be able to illuminate and observe a region laterally at the distal end of the hollow shank. The instrument channel 6 running longitudinally in the hollow shank 1 comprises a distal end section 6a running laterally deflected and before this a curvature section 6b which in any case is formed flexible so that the section 6a can be pivoted when the instrument channel is moved in the longitudinal direction of the hollow shank by way of pushing its proximal operating part 7 forwards and backwards in the hollow shank, as is indicated with the double arrow 11. The end 6c of the end section 6a of the instrument channel 6 is mounted in an articulated manner in a radial passage 12 in the circumferential wall region 13 of the distal closing part 14 of the hollow shank 1. The curved section 6b and the end section 6a laterally deflect the auxiliary instrument 8 when the instrument is guided through the channel 6. The articulated mounting of the end 6c is schematically represented in FIG. 2 and is indicated at 15. The instrument channel 6 is displaceably guided in the hollow shank 1 preferably in guiding means. These guiding means may for example consist of one or more tubular inserts 16. Such guiding means are particularly advantageous when it is the case of an endoscope with a generally flexible shaft construction. It is then ensured that the instrument channel can be moved in the longitudinal direction of the hollow shank in a defined manner.

Figure 3:
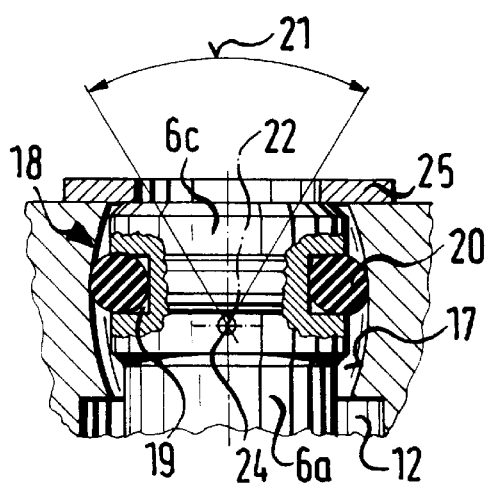
FIG. 3: a part sectional representation according to the detail A in FIG. 2 in an even larger scale.

As can be recognized best from FIG. 3, the radial passage 12 of the circumferential wall region 13 comprises a circumferential-like concave bearing surface 17 on which a sliding formation 18 of the end 6c of the instrument channel 6 pivotably bears. The formation 18 may e.g. be formed such that the end 6c comprises a circumferential groove 19 in which an elastic ring element 20 is located, e.g. a rubber ring. In particular due to the concave bearing surface 17 the end 6c of the instrument channel 6 pivots within an angular region which is indicated at 21. The pivoting of the end 6c with this is effected about an axis 22 which runs essentially transversely to the longitudinal axis 23 of the hollow shank 1.

In order to exactly fix the pivoting of the end 6c of the instrument channel 6 about the pivoting axis 22, i.e. in a plane which corresponds to the longitudinal extension of the hollow shank 1, there may be provided two bearing pins 24 which lie diametrically opposite transversely to the longitudinal direction of the hollow shank and which are flush with one another. These engage on the one side into the distal end 6c and on the other side into the walling 13 of the radial passage 12 and are rigidly arranged either in the one or the other part, i.e. unmovably arranged, whilst they bear pivotingly movable in the respective other part.

As has already been previously mentioned the formation 18 gliding on the concave circumferential surface 17, apart from guiding the insert 6c may also assume a sealing function. In the case that this is not desirable also separate sealing means may be provided which avoid a penetration of dirt particles into the inside of the hollow shank 1 through the radial passage 12. Such means may e.g. consist of annular disks as are indicated at 25 in FIG. 3. In this case the gliding formation 18 may have a different construction from that which is shown in FIG. 3, with which it is possible, without the presence of separate sealing means 25, for dirt particles to penetrate into the hollow shank 1.

In particular, from the FIGS. 2 and 3 and the parts of the description relating to these, it is clear that the section of an auxiliary instrument protruding distally from the hollow shank may be pivoted also beyond an angle of 90° in a retrograde direction. This is particularly clear from FIG. 2, wherein the 90° angle is indicated at 26.

Figure 4:
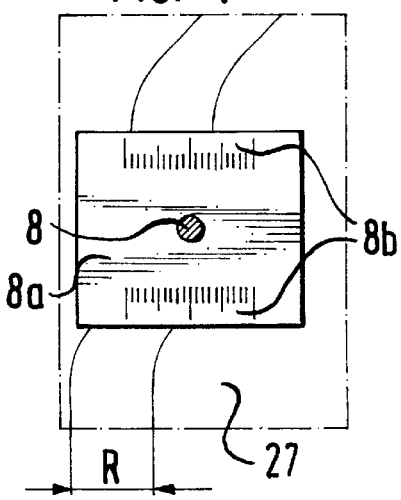
FIG. 4: a measuring probe in a measuring position, seen from the lateral exit view of the endoscope.
Figure 5:
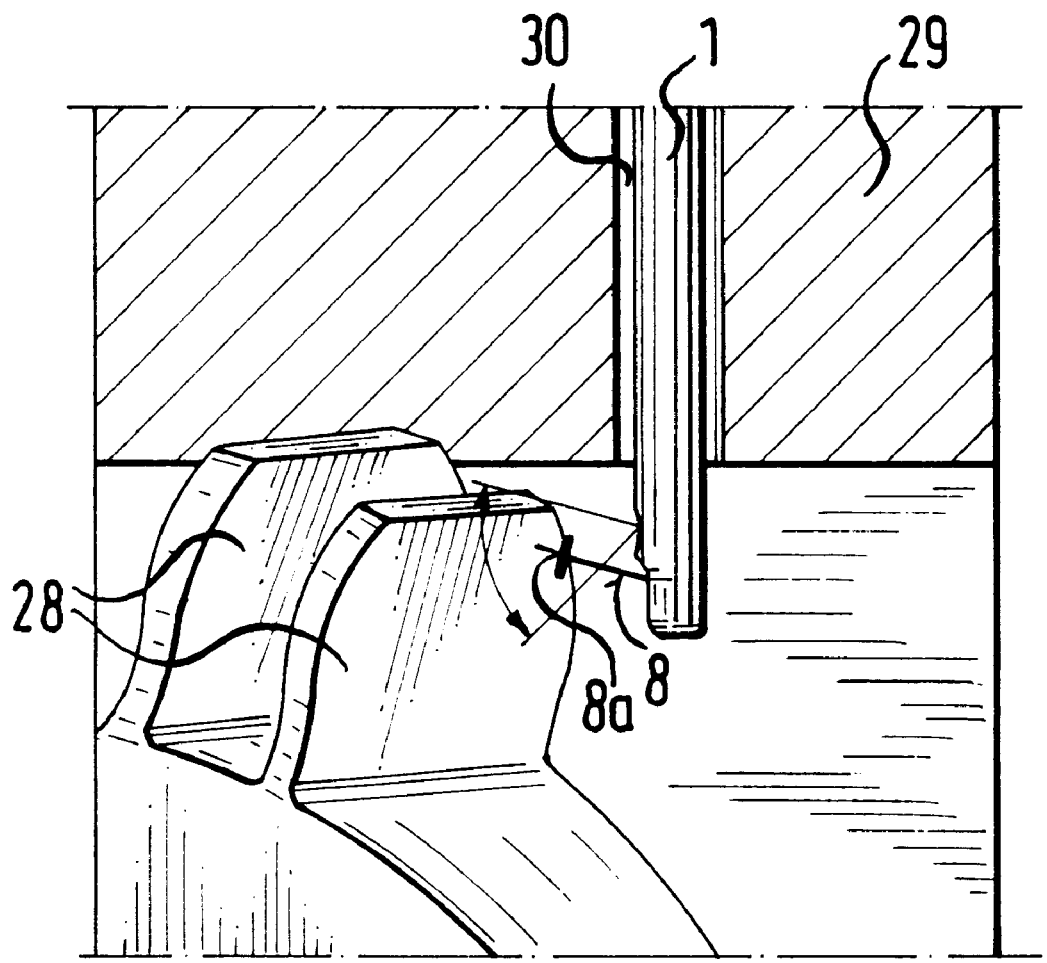
FIG. 5: the measuring probe in the measuring position with a bladed engine in a lateral view.

FIG. 4 shows the measuring probe 8 as an example auxiliary instrument, in the measuring position. The measuring probe comprises a measuring plate 8a with length measuring scales 8b in order for example to measure out fractures R or other damaged regions in a body 27, surface or likewise in a cavity. Such a measuring plate 8a may from now on also be introduced into regions of cavities which have hitherto been difficult to access or were unaccessible. For this by way of example FIG. 5 clearly shows that the tip regions of blades of a turbine engine may be easily viewed and possible damage may be clearly determined and may be exactly measured out with respect to their extension. The engine housing 29 for this needs only to have an inspection hole 30 which is very small in diameter. Another auxiliary instrument which is not shown may be a spray nozzle means in order to be able to incorporate a working agent, e.g. a fluorescing agent, into the cavity concerned.

Although the above described endoscope is preferably applied with technical examinations it is however also possible to apply this endoscope to the examination of body cavities in living beings. Furthermore the described endoscope may be provided with a generally rigid hollow shank as well as with a flexible hollow shank.

I claim:

1. An endoscope for use in a body cavity in conjunction with a flexible auxiliary instrument, comprising:

a hollow shank having a distal end region defined by a distal circumferential wall region having a radial passage, a distal lateral opening and an internal guiding region for guiding the auxiliary instrument therethrough such that the auxiliary instrument exits through said distal lateral opening;

optic viewing means positioned in said hollow shank for observing the body cavity when the hollow shank is proximal to the cavity; and a separate adjustable instrument channel axially slidably arranged in said internal guiding region for receiving the auxiliary instrument, said instrument channel having a flexible curvature section and a laterally running end section having an end portion, wherein said end portion is pivotably and articulably mounted in said radial passage of said distal circumferential wall region so that sliding said instrument channel axially in said hollow shank results in flexing of said curvative section and pivoting of the end portion whereby the auxiliary instrument is laterally deflected when guided through the hollow shank.

2. The endoscope of claim 1, wherein said radial passage comprises a circumferential concave bearing surface, and wherein said end portion of said end section comprises a formation in glidable contact with said concave bearing surface.

3. The endoscope of claim 1, wherein said gliding formation comprises a circumferential groove having an elastic ring element positioned therein.

4. The endoscope of claim 1, wherein said hollow shank comprises a longitudinal axis, and wherein said end section of said instrument channel comprises a pair of bearing pins having a respective first side and a second side, positioned transversely and diametrically opposite to said longitudinal axis, said pair of bearing pins being flush with one another, wherein on said first side said pair of bearing pins engage said end section, and wherein on said second side, said pair of bearing pins engage said radial passage wall.

5. The endoscope of claim 1, further comprising sealing means positioned in said hollow shank between said radial passage and said end section of said instrument channel.

6. The endoscope of claim 1, wherein said hollow shank further comprises internal guiding means positioned with said hollow shank for receiving said instrument channel to enable longitudinal displacement of said instrument channel within said hollow shank.

\* \* \* \* \*